United States Patent
Yoshino et al.

[11] Patent Number: 5,176,889
[45] Date of Patent: Jan. 5, 1993

[54] METHOD AND APPARATUS FOR TREATMENT OF NF$_3$ GAS

[75] Inventors: Akira Yoshino; Takakazu Tomoda, both of Osaka, Japan

[73] Assignee: Daidousanso Co., Ltd., Osaka, Japan

[21] Appl. No.: 827,538

[22] Filed: Jan. 30, 1992

Related U.S. Application Data

[63] Continuation of Ser. No. 593,721, Oct. 4, 1990, abandoned.

[30] Foreign Application Priority Data

Jul. 9, 1990 [JP] Japan .................. 2-182183

[51] Int. Cl.$^5$ .................. C01B 21/083; B01D 53/04
[52] U.S. Cl. .................. 423/240 S; 55/75; 55/71; 423/406
[58] Field of Search .......... 423/240 S, 245.1, 406; 55/75, 71

[56] References Cited

U.S. PATENT DOCUMENTS

| | | | |
|---|---|---|---|
| 4,053,557 | 10/1977 | Kageyama | 423/240 S |
| 4,092,403 | 5/1978 | Rectenwald et al. | 423/240 S |
| 4,156,598 | 5/1979 | Woytek et al. | 423/406 |
| 4,193,976 | 3/1980 | Lileck et al. | 423/406 |
| 4,215,096 | 7/1980 | Sinha et al. | 423/240 S |
| 4,673,558 | 6/1987 | Senoue et al. | 423/240 S |
| 4,820,681 | 4/1989 | Chang et al. | 502/418 |
| 4,933,158 | 6/1990 | Aritsuka et al. | 423/240 S |
| 4,948,571 | 8/1990 | Harada et al. | 423/240 S |

FOREIGN PATENT DOCUMENTS

| | | | |
|---|---|---|---|
| 2573324 | 5/1986 | France | 423/240 S |
| 61-287424 | 12/1986 | Japan | 423/240 S |
| 62-237929 | 10/1987 | Japan | 423/406 |
| 63-151608 | 6/1988 | Japan | 423/240 S |

Primary Examiner—John Niebling
Assistant Examiner—Brian M. Bolam
Attorney, Agent, or Firm—Armstrong & Kubovcik

[57] ABSTRACT

In accordance with this invention, a waste gas containing toxic NF$_3$ gas is contacted with a honeycomb structure of a carbonaceous material to thereby convert NF$_3$ into nontoxic CF$_4$ and H$_2$ gases with high efficiency.

2 Claims, 2 Drawing Sheets

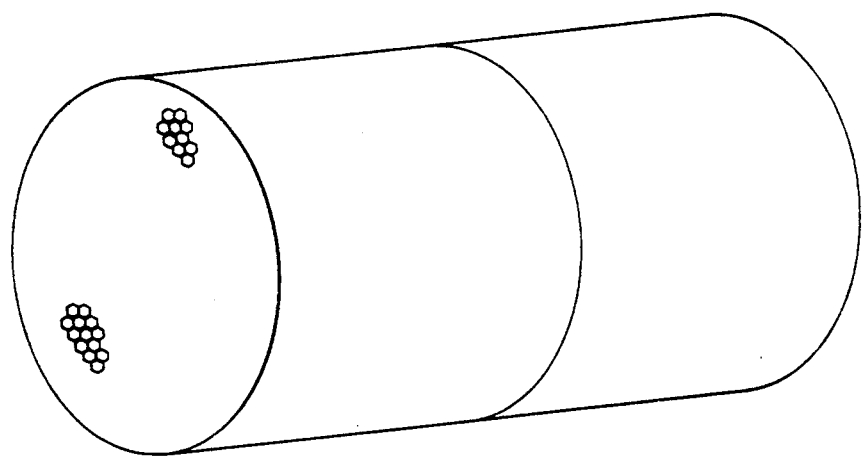
FIG. 1
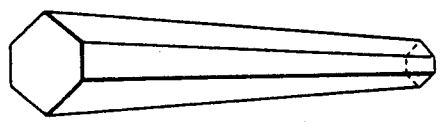
FIG. 2
FIG. 3
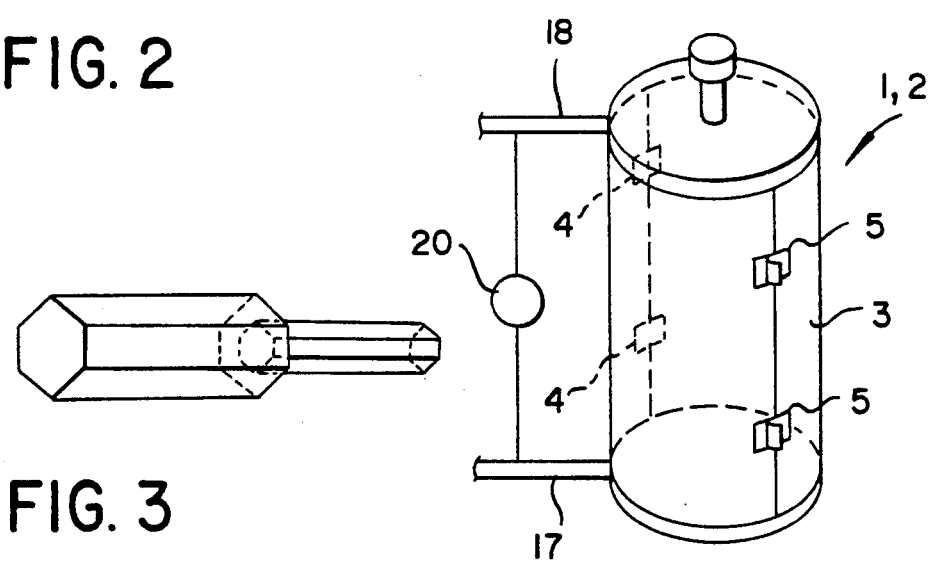
FIG. 5

METHOD AND APPARATUS FOR TREATMENT OF NF₃ GAS

This application is a continuation of application Ser. No. 07/593,721 filed Oct. 4, 1990, now abandoned.

FIELD OF THE INVENTION

The present invention relates to a method and an apparatus for the treatment of a $NF_3$-containing waste gas which comprises converting $NF_3$ to $CF_4$ and $N_2$ gases.

BACKGROUND OF THE INVENTION $NF_3$ gas is generally used as the dry etching gas or the cleaning gas in the manufacture of semiconductors. Thus, the etching of silicon with an ionized reactive gas in $NF_3$ discharge gives volatile reaction products and this is an advantage because, unlike the earlier method of etching in a fluorocarbon plasma, chances for fouling of wafer surfaces with reaction by products, e.g. carbon (C) and sulfur (S), are eliminated and accordingly the etching speed is expedited. For this reason, $NF_3$ gas is used more often in these days but since this gas is highly stable at ordinary temperature, it is not decomposed in the atmosphere, thus, causing various adverse effects on living matter. Moreover, although it is not inflammable, $NF_3$ gas is toxic with a maximum allowable concentration of 10 ppm. Therefore, disposal of the waste gas presents a major problem.

The applicant of the present invention already proposed a method for treating $NF_3$ gas which comprises reacting a $NF_3$-containing waste gas with a mass of carbon, such as charcoal, at a high temperature to convert $NF_3$ into non-toxic $CF_4$ and $N_2$ gases Japanese Patent Application No. 78863/1986). For carrying this method into practice, granular carbon as the mass of carbon is packed into a cylindrical reactor and said $NF_3$-containing waste gas is passed through the layer of granular carbon so as to convert $NF_3$ to non-toxic $CF_4$ and $N_2$ gases in the process. This method is advantageous in that $NF_3$ is converted to non-toxic $CF_4$ and $N_2$ and that even if $O_2$ is contained in the $NF_3$ waste gas, it is converted to $CO_2$ gas. Another known technique for treating a $NF_3$-containing waste gas comprises the use of silicon as a catalyst. However, this method has the disadvantage that it requires an additional step for treatment of poisonous $SiF_4$. Recently, $O_2$ has been used in combination with $NF_3$ for enhanced cleaning effect but when this silicon catalyst method is applied in such cases, $O_2$ reacts with silicon to give $SiO_2$, which is a solid, and this $SiO_2$ tends to plug the piping. In the abovementioned method employing a mass of carbon as a catalyst as previously proposed by the present applicant, $NF_3$ is directly converted to non-toxic $CF_4$ and $N_2$ gases and even if $O_2$ is contained in the $NF_3$-containing waste gas, $O_2$ reacts with carbon to give $CO_2$ gas, thus causing no such troubles as plugged piping. However, when a production-scale plant was constructed and operated, the following disadvantage was discovered. As the grain size of granular carbon is gradually decreased as the reaction continues, the intergrain gaps are progressively narrowed to increase the flow resistance of the $NF_3$-containing waste gas, with the result that the pressure differential between the inlet and outlet ends of the reactor is also progressively increased. Therefore, the back pressure (pressure at the outlet end) of the semiconductor manufacturing equipment connected to reactor through a pipeline is also increased and accordingly the internal pressure of the semiconductor manufacturing equipment is also increased to interfere with stable operation. In the above apparatus, the degree of consumption of granular carbon is ascertained by detecting the top level of the carbon packing in the cylindrical reactor with a level gauge utilizing a laser beam and the reactor is refilled with granular carbon when the top level falls below a reference level. In this apparatus, the above refilling results in an increased thickness of the carbon layer and the intergrain gaps are decreased (dust carbon enters into the gaps between grains) so that the flow resistance of the $NF_3$-containing waste gas is sharply increased to cause a rapid elevation of the back pressure of the semiconductor manufacturing equipment, thus interfering with stable operation.

OBJECTS AND SUMMARY OF THE INVENTION

The object of the present invention is to provide a method and an apparatus for treating $NF_3$ gas which is not accompanied by a sharp increase in pressure differential due to attrition or exchange of the carbon catalyst The present invention is, therefore, directed to a method of converting a $NF_3$-containing waste gas to nontoxic $CF_4$ and $N_2$ gases with the aid of a carbonaceus material, which comprises passing the $NF_3$-containing waste gas through a multiplicity of openings in a honeycomb structure of a carbonaceus material to thereby let the $NF_3$ gas contact the carbon constituting the walls defining said openings. In a second aspect, the present invention relates to an apparatus for practicing the above method, which comprises a reactor unit which can be opened and closed and a honeycomb structure of carbon which is replaceably accommodated in said reactor unit. In accordance with the present invention, a $NF_3$-containing waste gas is introduced into the multiplicity of openings in said honeycomb structure of carbon to let the gas contact the carbon walls defining said openings for efficient conversion of $NF_3$ gas into $CF_4$ and $N_2$ gases. In this treatment system, the consumption of carbon due to reaction results in enlargement of the openings in said honey-comb structure. Therefore, contrary to the event in the previous system, the attrition of catalyst carbon reduces the aforesaid pressure diffential in the present invention. When the pressure differential is diminished beyond a predetermined threshold, the honeycomb structure is replaced with a fresh one. However, since the honeycomb structure originally has said multiplicity of through openings and the openings are not plugged with fine particulate carbon, it does not happen that exchange of the honeycomb structure ever causes a sudden increase in said pressure differential.

BRIEF DESCRIPTION OF THE DRAWINGS

FIG. 1 is an elementary view showing the honeycomb structure used in accordance with the present invention;

FIG. 2 is a diagrammatic representation of each of the multiple openings in the honeycomb structure;

FIG. 3 is a diagrammatic representation of another configuration of said openings;

FIG. 5 is an elementary view on exaggerated scale showing the reactor unit of the apparatus.

DETAILED DESCRIPTION OF THE INVENTION

Figure 4:
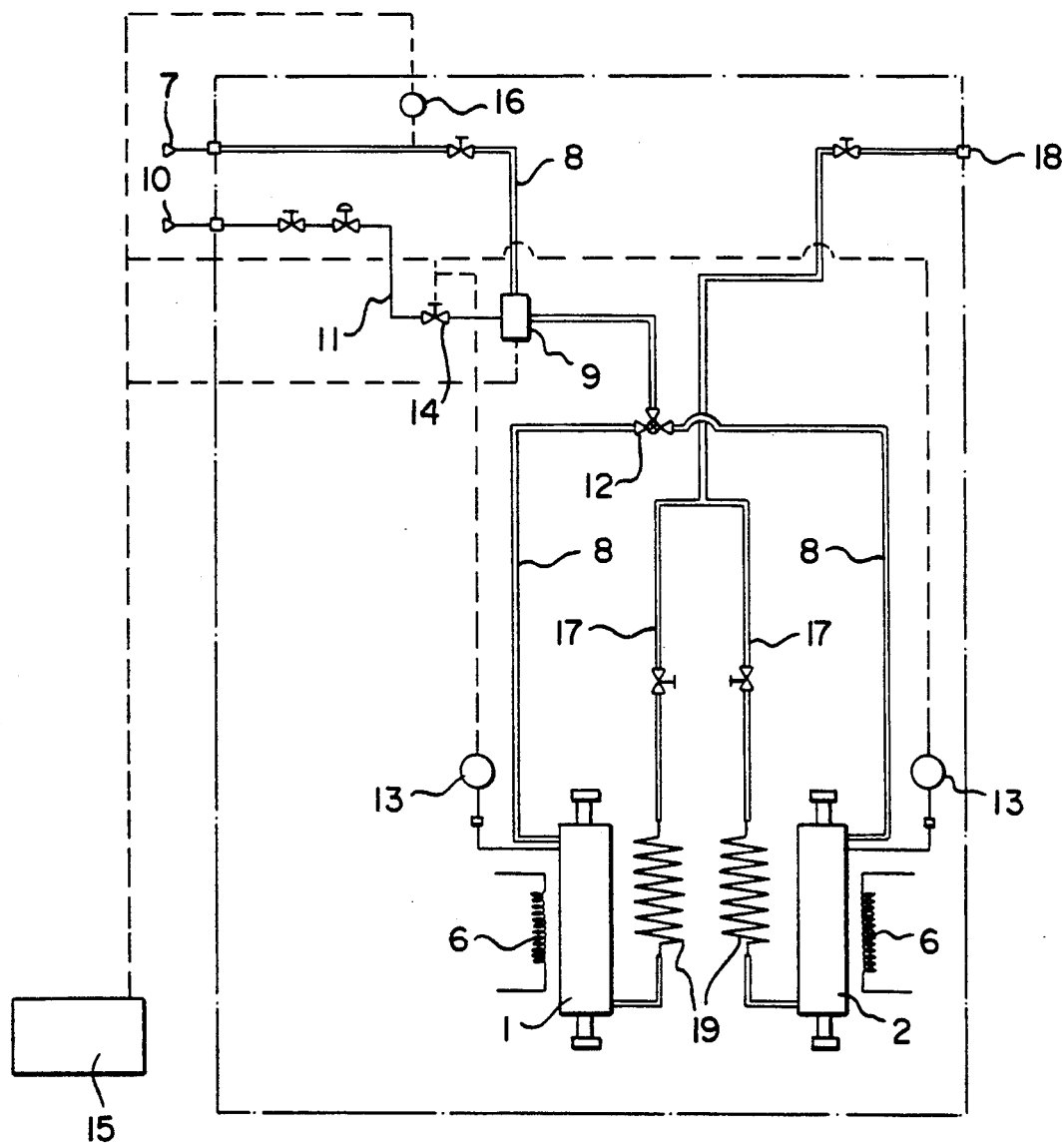
FIG. 4 is a schematic view illustrating an example of the apparatus for treating a $NF_3$-containing waste gas in accordance with the invention.

In the present invention, a $NF_3$-containing waste gas is contacted with a honeycomb structure of carbonaceus material at a high temperature to convert $NF_3$ into $CF_4$ and $N_2$.

The reaction between $NF_3$ gas and carbon can be written as

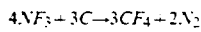

$$4NF_3 + 3C \rightarrow 3CF_4 + 2N_2$$

The reaction temperature is preferably between about 300° to 600° C. If the temperature is below 300° C., $NF_3$ will be adsorbed on the carbon and the product carbon tetrafluoride ($CF_4$) will not easily be desorbed. Conversely if the temperature exceeds about 600° C., corrosion of the reactor unit will be markedly accelerated and the heat of reaction be hardly controllable. Therefore, the term 'high temperature' as used herein with reference to the temperature at which the $NF_3$-containing waste gas is contacted with the catalyst carbon means any temperature within the range of 300° and 600° C.

The $NF_3$ concentration of the waste gas to be treated in accordance with the present invention may range widely from a low concentration of the ppm order to a high concentration of, for example, 100 percent by volume. Since the above reaction is an exothermic reaction, the reactor temperature is increased too high when a waste gas containing $NF_3$ in a high concentration, for example 40 percent by volume or higher, is treated. For the treatment of a waste gas containing such a high concentration of $NF_3$, an inert gas such as $N_2$ gas may be used as a carrier gas to lower the $NF_3$ concentration to about 30 percent by volume and to thereby prevent the excess temperature buildup in the reactor. Of course, such an inert gas may optionally be used as the carrier gas for waste gases containing $NF_3$ in low concentrations.

Regarding the honeycomb structure of carbonaceus material, its through openings generally have a diameter of 0.1 to 15 mm and a length of 10 cm to 5 m, preferably 1 to 2 m. Generally speaking, a honeycomb structure having long through openings is used for a $NF_3$-rich gas, while a honeycomb structure having comparatively short openings for a $NF_3$-lean gas.

The honeycomb structure of carbon can be manufactured by sintering fine particles of pure carbon not containing water, for instance. The configuration of the honeycomb structure is generally cylindrical so that it may be easily installed in a reactor, which may also be a cylindrical member, with said multiplicity of openings being oriented in the axial direction of the reactor unit. The through openings in the honeycomb structure are generally of constant diameter from the inlet end (left-handed side in FIG. 1) to the outlet end (right-handed side). However, the openings may be gently tapered from the inlet end toward the outlet end as illustrated in FIG. 2. Furthermore, as illustrated in FIG. 3, each opening may be reduced in diameter at an intermediate position along its length in the form of a stepped opening. Similarly, it may also be a multiple-stepped opening. When such configurations are used for the multiple openings, the waste gas is caused to swirl within the openings so that the efficiency of contact between the wall-defining carbon and the $NF_3$-containing waste gas is improved. It should be understood that the sectional configuration of the opening need not necessarily be hexagonal as illustrated but may for example be circular, triangular or square.

When a $NF_3$-rich waste gas is treated with the above-mentioned honeycomb structure, the mixing ratio of inert gas to waste gas need not be determined by detecting the $NF_3$ concentration beforehand but paying attention to the fact pointed out above that the reaction of a $NF_3$-rich gas results in a sharp increase in the internal temperature of the reactor, it can be so arranged that the internal temperature is automatically detected and the mixing ratio of inert gas to waste gas is accordingly controlled (The proportion of the inert gas is increased as the temperature rises and is decreased as the temperature falls).

To provide an elongated honeycomb structure of great length, a plurality of units of a short honeycomb structure may be joined one on top of another, whereby the cost of manufacture of honeycomb structures can be decreased.

PREFERRED EMBODIMENTS

An example of the apparatus for treatment of a $NF_3$-containing gas in accordance with the present invention is illustrated in FIG. 4. This apparatus includes a couple of cylindrical reactor unit 1 and 2 in juxtaposed positions. Disposed in each of the reactor units is a honeycomb structure of carbon, which is illustrated in FIG. 1, with its multiplicity of through openings oriented in the longitudinal or axial direction (the up-and-down direction in FIG. 4) of the reactor unit. The bottom of said honeycomb structure is supported by a collar (not shown) formed on the inner circumferential surface of the cylinder. The mounting and dismounting of the honeycomb structure with respect to the reactor unit 1 or 2 can be carried out by opening the trunk portion of the reactor unit 1 or 2. Thus, as illustrated in FIG. 5, the trunk portion 3 of each reactor unit can be swung open and closed about hinges 4. Indicated at 5 are metals used for retaining two members of the trunk portion in closed position. The reference numeral 20 represents a differential pressure gauge for measuring the pressure differential between the inlet and outlet ends of each reactor unit 1 or 2. As shown in FIG. 4, each of these reactor units 1 and 2 is provided with an electric resistance heater 6 and a pipeline 8 communicating the reactor unit to an inlet 7 for introducing a $NF_3$-containing waste gas. A gas mixer 9 is disposed upstreams of the pipeline 8 which is communicating with an inert gas pipeline 11 extending from the inert gas inlet 10.

Disposed in the pipeline downstreams of said gas mixer 9 is a three-way valve 12 at which the pipeline 8 is bifurcated into two branch lines communicating with the reactor units 1 and 2, respectively. Each of the reactor units 1 and 2 is provided with a control unit 13 including a temperature sensor so that when the internal temperature of either reactor unit 1 or 2 rises, a control valve 14 in the inert gas pipeline 11 is opened or the degree of its opening is increased to increase the rate of inflow of the inert gas and thereby lower the $NF_3$ concentration. Conversely when the internal temperature falls, the above-mentioned valve is throttled down to reduce or shut off the inflow of said inert gas. The reference numeral 15 represents a control box which, in response to a signal output from a $NF_3$ concentration sensor 16 disposed in the pipeline 8 closer to the waste gas inlet 7, adjusts the control valve 14 in the inert gas pipeline 11 to control the $NF_3$ concentration of the waste gas supplied to the reactor units 1 and 2. In this manner, this apparatus is not only provided with a control system such that the $NF_3$ concentration is controlled according to the internal temperature of the reactor units 1 and 2 but also a control system centered around said control box 15.

Usually, the valve 14 is controlled by the control unit 13 including a temperature sensor which is directly associated with the reactor unit 1 or 2 and the control system centered around the control box 15 is used in the event of a failure of the first-mentioned control system. In the apparatus thus described, the $NF_3$-containing waste gas enters the apparatus from the inlet 7 and flows through the pipeline 8 and the gas mixer 9 and enters into the three-way valve 12. In operation, either one of the reactor units 1 and 2 is put into service, while the other unit stands by. Therefore, the waste gas enters into the reactor 1, for instance, where it contacts and reacts with the carbon within the through openings in the honeycomb structure, whereby $NF_3$ is converted to $CF_4$ and $N_2$. These nontoxic gases are exhausted from the exhaust port 18 through the processed gas outlet 17. As the honeycomb structure is consumed in the above treatment of the $NF_3$-containing waste gas and the differential pressure reading on the differential pressure gauge 20 drops below a preset level, the reactor 1 or 2 is opened as illustrated in FIG. 5 and the honeycomb structure is replaced with a fresh honeycomb structure. Referring to FIG. 4, the reference numeral 19 represents a cooling coil and the one-dot-chain line indicates an outer structure housing the above components and parts.

The following examples illustrate the treatment of $NF_3$-containing gases which was actually performed.

EXAMPLE 1

$NF_3$ of 100% concentration was treated with the apparatus illustrated in FIG. 4 (incorporating the honeycomb structure having a multiplicity of through openings of the configuration shown in FIG. 2) at a reaction temperature of 400° C., a reaction pressure of 1 atmosphere and a flow rate of SV=30~250 l/hr. The results are shown in Table 1. It should be understood that SV=flow rate (l/hr)/packing volume (l). It will be apparent from Table 1 that the $NF_3$ concentration is reduced to a level of 5 ppm (a detection limit of gas chromatography).

EXAMPLE 2

$NF_3$ gas was diluted with $N_2$ gas to a concentration of 3% and treated with the apparatus illustrated in FIG. 4 (incorporating a honeycomb structure having a multiplicity of openings of constant diameter). The results are shown in Table 2. It is apparent that a $NF_3$-lean gas can also be thoroughly treated.

EXAMPLE 3

A mixed gas consisting of 4% $NF_3$, 1% chlorine ($Cl_2$) and 1% hydrogen chloride (HCl) was treated with the apparatus of FIG. 4 (incorporating a honeycomb structure having a multiplicity of through openings of the configuration illustrated in FIG. 3). The results are shown in Table 3. It is apparent that even a Cl-containing gas can also be successfully treated without interference with the reaction.

TABLE 1

| | (100% $NF_3$) | | | |
|---|---|---|---|---|
| | Operating conditions | | $NF_3$ concentration of | Principal |
| Flow rate SV (l/Hr) | Temperature, °C. | Pressure, atm | feed gas ppm | reaction products |
| 30 | 400 | 1 | ND (≦5 ppm) | $N_2$, $CF_4$, $C_2$, $F_6$ |
| 140 | 400 | 1 | ND (≦5 ppm) | $N_2$, $CF_4$, $C_2$, $F_6$ |
| 500 | 400 | 1 | ND (≦5 ppm) | $N_2$, $CF_4$, $C_2$, $F_6$ |

TABLE 2

| | (3% $NF_3$) | | | |
|---|---|---|---|---|
| | Operating conditions | | $NF_3$ concentration of | Principal |
| Flow rate SV (l/Hr) | Temperature, °C. | Pressure, atm | feed gas ppm | reaction products |
| 30 | 400 | 1 | ND (≦5 ppm) | $N_2$, $CF_4$, $C_2$, $F_6$ |
| 300 | 400 | 1 | ND (≦5 ppm) | $N_2$, $CF_4$, $C_2$, $F_6$ |
| 600 | 400 | 1 | ND (≦5 ppm) | $N_2$, $CF_4$, $C_2$, $F_6$ |
| 2000 | 400 | 1 | ND (≦5 ppm) | $N_2$, $CH_4$, $C_2$, $F_6$ |

TABLE 3

| | (4% $NF_3$ + 1% $Cl_2$ + 1% HCl) | | | |
|---|---|---|---|---|
| | Operating conditions | | $NF_3$ concentration of | Principal |
| Flow rate SV (l/Hr) | Temperature, °C. | Pressure, atm | feed gas ppm | reaction products |
| 600 | 400 | 1 | ND (≦5 ppm) | $N_2$, $CF_4$, $C_2$, $F_6$ ($Cl_2$, HCl) |
| 1100 | 400 | 1 | ND (≦5 ppm) | $N_2$, $CF_4$, $C_2$, $F_6$ ($Cl_2$, HCl) |
| 1900 | 400 | 1 | ND (≦5 ppm) | $N_2$, $CF_4$, $C_2$, $F_6$ ($Cl_2$, HCl) |

In accordance with the present invention employing a honeycomb structure of carbon having a multiplicity of through openings, the attrition of the honeycomb structure by the reaction with $NF_3$ results in an increase in the diameter of said openings. Therefore, unlike in the conventional system, the consumption of the carbon does not lead to an increased pressure differential but rather decreases the pressure differential. Therefore, the back pressure of the semiconductor manufacturing equipment connected to the apparatus of the invention is not increased and, hence, the variation in the internal pressure of the equipment is precluded, thus providing for stable manufacturing operation. In the present invention, when the above-mentioned pressure differential is diminished beyond a given threshold level, the honeycomb structure is replaced with a fresh one. However, since the honeycomb structure originally has a multiplicity of through openings and these openings are not plugged with fine carbon dust, there is no risk for a sharp change in said pressure differential on replacement of the honeycomb structure.

What is claimed is:

1. A method for converting gaseous $NF_3$ into $CF_4$ and $N_2$ gases, comprising passing a $NF_3$ containing gas through a multiplicity of openings in a honeycomb structure of carbon at a temperature of about 300° C. to about 600° C., whereby said $NF_3$ containing gas reacts with walls of carbon defining said openings.

2. The method for treating $NF_3$ gas as claimed in claim 1 wherein said openings have a diameter of 0.1 to 15 mm.

* * * * *